(12) United States Patent
Ledany

(10) Patent No.: US 10,737,107 B2
(45) Date of Patent: Aug. 11, 2020

(54) LED-LASER BIOMAGNETIC WAVE THERAPY DEVICE

(71) Applicant: Ori Ledany, Las Vegas, NV (US)

(72) Inventor: Ori Ledany, Las Vegas, NV (US)

(*) Notice: Subject to any disclaimer, the term of this patent is extended or adjusted under 35 U.S.C. 154(b) by 237 days.

(21) Appl. No.: 15/877,307

(22) Filed: Jan. 22, 2018

(65) Prior Publication Data
US 2018/0140860 A1 May 24, 2018

Related U.S. Application Data

(63) Continuation-in-part of application No. 14/681,871, filed on Apr. 8, 2015, now abandoned.

(60) Provisional application No. 61/976,857, filed on Apr. 8, 2014, provisional application No. 62/448,562, filed on Jan. 20, 2017.

(51) Int. Cl.
A61H 23/00 (2006.01)
A61N 2/00 (2006.01)
A61N 5/06 (2006.01)
A61H 23/02 (2006.01)
A61H 39/00 (2006.01)
A61H 15/00 (2006.01)
A61N 2/06 (2006.01)
A61N 5/067 (2006.01)

(52) U.S. Cl.
CPC ............ *A61N 2/008* (2013.01); *A61H 23/00* (2013.01); *A61H 23/02* (2013.01); *A61H 23/0254* (2013.01); *A61H 39/00* (2013.01); *A61N 2/002* (2013.01); *A61N 5/06* (2013.01); *A61H 15/0085* (2013.01); *A61H 2039/005* (2013.01); *A61H 2201/0153* (2013.01); *A61H 2201/0157* (2013.01); *A61H 2201/0169* (2013.01); *A61H 2201/10* (2013.01); *A61H 2201/1207* (2013.01); *A61H 2201/1657* (2013.01); *A61H 2201/50* (2013.01); *A61H 2201/5005* (2013.01); *A61H 2201/5025* (2013.01); *A61N 2/06* (2013.01); *A61N 2005/067* (2013.01); *A61N 2005/0644* (2013.01); *A61N 2005/0651* (2013.01); *A61N 2005/0652* (2013.01)

(58) Field of Classification Search
CPC .... A61H 15/02; A61H 2201/10; A61H 23/00; A61N 2/06; A61N 2/002; A61N 2/008; A61N 5/06; A61N 2005/067
See application file for complete search history.

(56) References Cited

U.S. PATENT DOCUMENTS

| 5,382,222 A | 1/1995 | Yih-Jong |
| 5,632,720 A | 5/1997 | Kleitz |
| 5,782,858 A | 7/1998 | Cheng |

(Continued)

*Primary Examiner* — Justine R Yu
*Assistant Examiner* — Christopher E Miller
(74) *Attorney, Agent, or Firm* — Moss & Barnett; Michael A. Bondi

(57) ABSTRACT

A portable LED-laser biomagnetic waves therapy device including a body portion, a head portion, a plurality of magnets, a plurality of LED lights, a laser and a power mechanism. The head portion is attachable to an end of the body portion. The plurality of magnets is mounted to at least one of the body portion and the head portion. The plurality of LED lights is mounted to at least one of the body portion and the head portion. The laser is mounted to at least one of the body portion and the head portion. The power mechanism is operably attached to the plurality of LED lights and the laser.

17 Claims, 8 Drawing Sheets

(56) References Cited

U.S. PATENT DOCUMENTS

| | | | |
|---|---|---|---|
| 6,001,055 A * | 12/1999 | Souder | A61N 2/008 600/9 |
| 6,123,657 A * | 9/2000 | Ishikawa | A61N 2/12 600/9 |
| 6,126,589 A * | 10/2000 | Brooks | A61N 2/06 600/15 |
| 6,461,377 B1 | 10/2002 | An | |
| 6,544,164 B1 * | 4/2003 | Fan | A44C 5/0023 600/15 |
| 6,558,310 B1 * | 5/2003 | Baermann | A61N 2/00 600/15 |
| 6,746,473 B2 * | 6/2004 | Shanks | A61N 5/0616 606/9 |
| 6,979,300 B1 | 12/2005 | Julian | |
| 7,803,104 B2 | 9/2010 | Sotiriou | |
| 8,257,242 B2 | 9/2012 | Sotiriou | |
| 8,936,542 B1 * | 1/2015 | Bates | A61N 2/002 600/9 |
| 9,126,034 B1 * | 9/2015 | Deroberts | A61N 5/0616 |
| 2002/0115903 A1 * | 8/2002 | Miyazaki | A61N 2/06 600/9 |
| 2004/0030370 A1 * | 2/2004 | Lytle | A61N 5/0616 607/89 |
| 2004/0106842 A1 | 6/2004 | Wang | |
| 2004/0260210 A1 | 12/2004 | Ella | |
| 2005/0015030 A1 * | 1/2005 | Bousfield | A61H 15/0085 601/113 |
| 2005/0045189 A1 * | 3/2005 | Jay | A61B 5/0059 128/898 |
| 2005/0070977 A1 | 3/2005 | Molina | |
| 2005/0131497 A1 | 6/2005 | Suzuki | |
| 2006/0047330 A1 * | 3/2006 | Whatcott | A61N 5/0616 607/89 |
| 2006/0253051 A1 | 11/2006 | Milne | |
| 2007/0027411 A1 | 2/2007 | Ella | |
| 2007/0073198 A1 * | 3/2007 | Koljaka | A61N 5/0613 601/15 |
| 2007/0073366 A1 * | 3/2007 | Porco | A61H 15/02 607/89 |
| 2007/0083074 A1 * | 4/2007 | Sotiriou | A61N 2/12 600/8 |
| 2007/0179333 A1 | 8/2007 | Bove | |
| 2007/0185553 A1 * | 8/2007 | Kennedy | A61N 5/0616 607/100 |
| 2008/0172045 A1 * | 7/2008 | Shanks | A61N 5/0616 606/3 |
| 2008/0214968 A1 * | 9/2008 | Milne | A61H 23/0263 601/15 |
| 2008/0246573 A1 * | 10/2008 | Souder | H01F 7/0294 335/306 |
| 2008/0262394 A1 * | 10/2008 | Pryor | A61H 7/007 601/15 |
| 2009/0005631 A1 | 1/2009 | Simenhaus | |
| 2009/0048557 A1 | 2/2009 | Yeshurun | |
| 2009/0088824 A1 * | 4/2009 | Baird | A61N 5/0616 607/90 |
| 2009/0234423 A1 | 9/2009 | Vetanze | |
| 2009/0270779 A1 | 10/2009 | Kurosu | |
| 2009/0287195 A1 | 11/2009 | Altshuler | |
| 2010/0049177 A1 * | 2/2010 | Boone, III | A61H 9/0057 606/9 |
| 2010/0081858 A1 * | 4/2010 | Sotiriou | A61N 2/12 600/13 |
| 2010/0121419 A1 * | 5/2010 | Douglas | A61N 5/0616 607/90 |
| 2010/0179456 A1 * | 7/2010 | Chen | A61H 15/00 601/18 |
| 2011/0032960 A1 * | 2/2011 | Gerlitz | A61N 5/0616 372/29.021 |
| 2011/0040235 A1 | 2/2011 | Castel | |
| 2011/0106067 A1 | 5/2011 | Geva | |
| 2011/0133872 A1 * | 6/2011 | Souder | H01F 7/0294 335/306 |
| 2011/0143286 A1 * | 6/2011 | Takada | A61F 9/00804 430/322 |
| 2011/0144410 A1 * | 6/2011 | Kennedy | A61B 18/203 600/2 |
| 2012/0209357 A1 | 8/2012 | Ha | |
| 2013/0030506 A1 * | 1/2013 | Bartolone | A61N 5/0616 607/89 |
| 2013/0046212 A1 | 2/2013 | Nichols | |
| 2014/0088337 A1 * | 3/2014 | Hedgecock | A61N 2/06 600/9 |
| 2014/0100410 A1 | 4/2014 | Balzer | |
| 2014/0114116 A1 | 4/2014 | Bae | |
| 2014/0128780 A1 | 5/2014 | Kennedy | |
| 2014/0194668 A1 * | 7/2014 | Hanson | A61N 2/004 600/9 |
| 2015/0045702 A1 | 2/2015 | Lin | |
| 2015/0150599 A1 | 6/2015 | Matsushita | |
| 2016/0158568 A1 * | 6/2016 | Uplaznik | A61N 5/0616 600/9 |

* cited by examiner

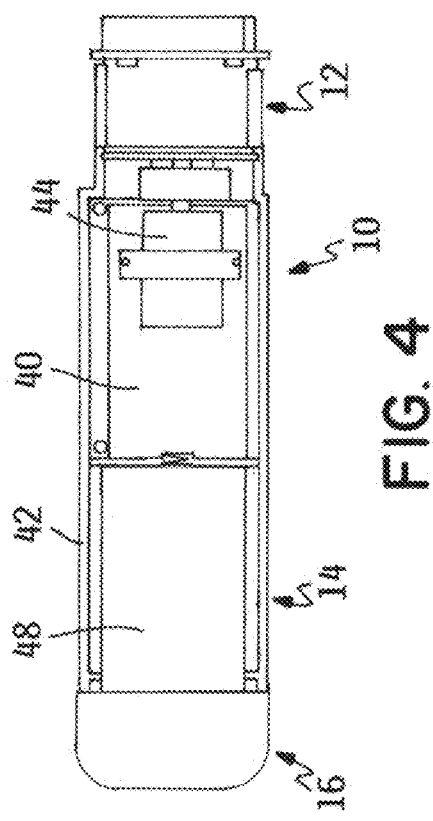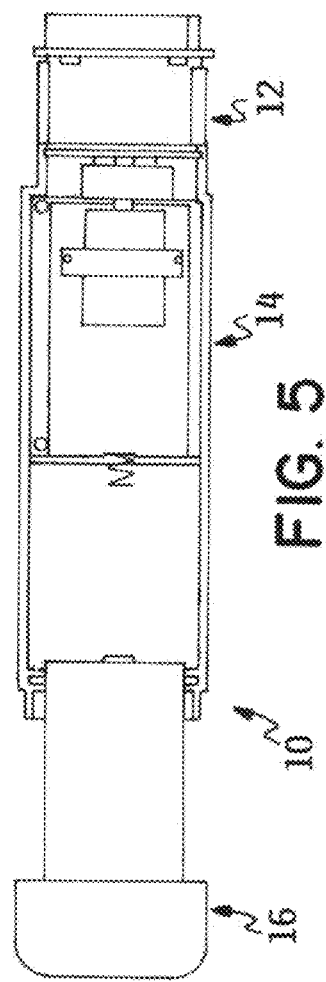

US 10,737,107 B2

LED-LASER BIOMAGNETIC WAVE THERAPY DEVICE

REFERENCE TO RELATED APPLICATION

This application is a continuation-in-part of U.S. application Ser. No. 14/681,871, filed on Apr. 8, 2015, which claims priority to Provisional Applic. No. 61/976,857, filed on Apr. 8, 2014, and claims priority to Provisional Applic. No. 62/448,562, filed on Jan. 20, 2017, the contents of which are incorporated herein by reference.

FIELD OF THE INVENTION

The invention relates to devices for treating soft tissue ailments in a human body. More particularly, the invention relates to an LED-laser biomagnetic wave therapy device.

BACKGROUND OF THE INVENTION

It is known that vibration therapy devices may be used to treat pain and aches of soft tissue to ease the physical ailments in a human body. One such portable vibration therapy device is disclosed in Ledany, U.S. Pat. No. 5,918,601.

SUMMARY OF THE INVENTION

An embodiment of the invention is directed to a portable LED-laser biomagnetic waves therapy device that includes a body portion, a head portion, a plurality of magnets, a plurality of LED lights, a laser and a power mechanism. The head portion is attachable to an end of the body portion. The plurality of magnets is mounted to at least one of the body portion and the head portion. The plurality of LED lights is mounted to at least one of the body portion and the head portion. The laser is mounted to at least one of the body portion and the head portion. The power mechanism is operably attached to the plurality of LEDs and the laser.

Another embodiment of the invention is directed to a portable LED-laser biomagnetic waves therapy device that includes a body portion, a head portion, a plurality of magnets, a plurality of LEDs, a laser, a power mechanism, a head cover and a resilient cover. The head portion is attachable to an end of the body portion. The head portion has a plurality of grooves formed in an outer surface thereof. The plurality of magnets is mounted to at least one of the body portion and the head portion. The plurality of LED lights is mounted to at least one of the body portion and the head portion. The laser is mounted to at least one of the body portion and the head portion. The power mechanism is operably attached to the plurality of LED lights and the laser. The head cover extends over at least part of the head portion on which the plurality of grooves is located. The head cover has a plurality of openings formed therein through which the head portion is visible. The resilient cover extends over at least a portion of the body portion.

Another embodiment of the invention is directed to a method of treating pain. A portable LED-laser biomagnetic waves therapy device is provided that includes a body portion, a head portion, a plurality of magnets, a plurality of LED lights, a laser and a power mechanism. The head portion is attachable to an end of the body portion. The plurality of magnets is mounted to at least one of the body portion and the head portion. The plurality of LED lights is mounted to at least one of the body portion and the head portion. The laser is mounted to at least one of the body portion and the head portion. The power mechanism is operably attached to the plurality of LED lights and the laser. The plurality of LED lights and the laser are activated with the power mechanism to cause light to be emitted therefrom. The portable LED-laser biomagnetic waves therapy device is positioned proximate a human body that is experiencing pain beneath the skin surface so that the light from the LED lights and the laser impinge upon the human body to cause a decrease in the pain.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4 is a sectional view of the portable LED-laser biomagnetic waves therapy device in an assembled configuration.

FIG. 5 is a sectional view of the portable LED-laser biomagnetic waves therapy device with an end cap partially inserted.

DETAILED DESCRIPTION OF THE INVENTION

Figures 1, 2:
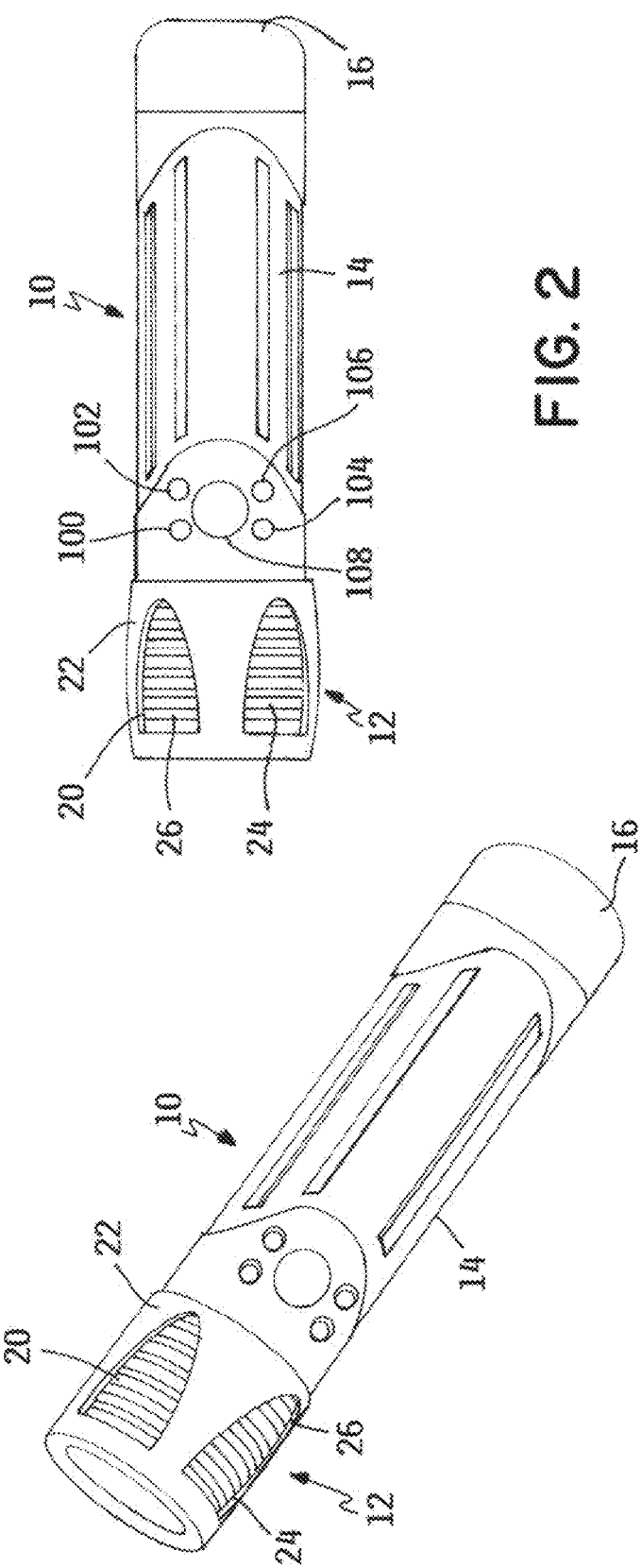
FIG. 1 is a perspective view of a portable LED-laser biomagnetic waves therapy device according to an embodiment of the invention.
FIG. 2 is a side view of the portable LED-laser biomagnetic waves therapy device.

An embodiment of the invention is directed to a portable LED-laser biomagnetic waves therapy device 10 that includes three main components a head unit 12, a body portion 14 and a bottom cap portion 16, as illustrated in the Figures.

In certain embodiments, a length of the portable LED-laser biomagnetic waves therapy device 10 may be about 6¾ inches. In certain embodiments, the head unit 12 and the body portion 14 may have a diameter of about 2 inches. In certain embodiments, the bottom cap portion 16 may have a diameter of about 1⅝ inches.

The head unit 12 may be removably attached to the body portion 14 with a thread mechanism. The head unit 12 may have a plurality of grooves 20 formed in an outer surface thereof.

At least a portion of a head cover 22 may be placed over the head unit 12. The head cover 22 may have at least one opening 26 formed therein. The opening 26 enables the areas of the head unit 12 that are beneath to be seen. Such a configuration may facilitate obtaining a vibration action by contact with the grooves 20 on the head unit 12.

The head cover 22 may be fabricated of soft plastic/rubber that is similar to the soft plastic material that is used on a toothbrush handle. The soft plastic material may create resistive friction.

Figure 6:
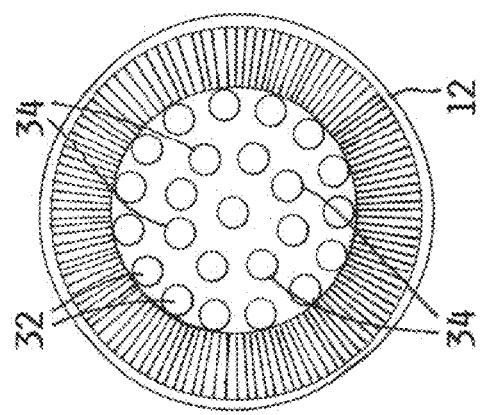
FIG. 6 is an end view of an embodiment of a head unit of the portable LED-laser biomagnetic waves therapy device.
Figure 7:
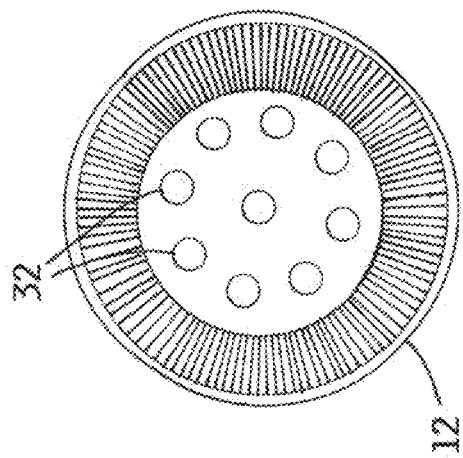
FIG. 7 is an end view of an alternative configuration of the head unit of the portable LED-laser biomagnetic waves therapy device.

An upper surface of the head cover 22, which is opposite the body portion 14, may have a plurality of grooves 24 formed therein, as illustrated in FIGS. 6 and 7. The grooves 24 may enhance the vibrating action of the device 10.

Figure 3:
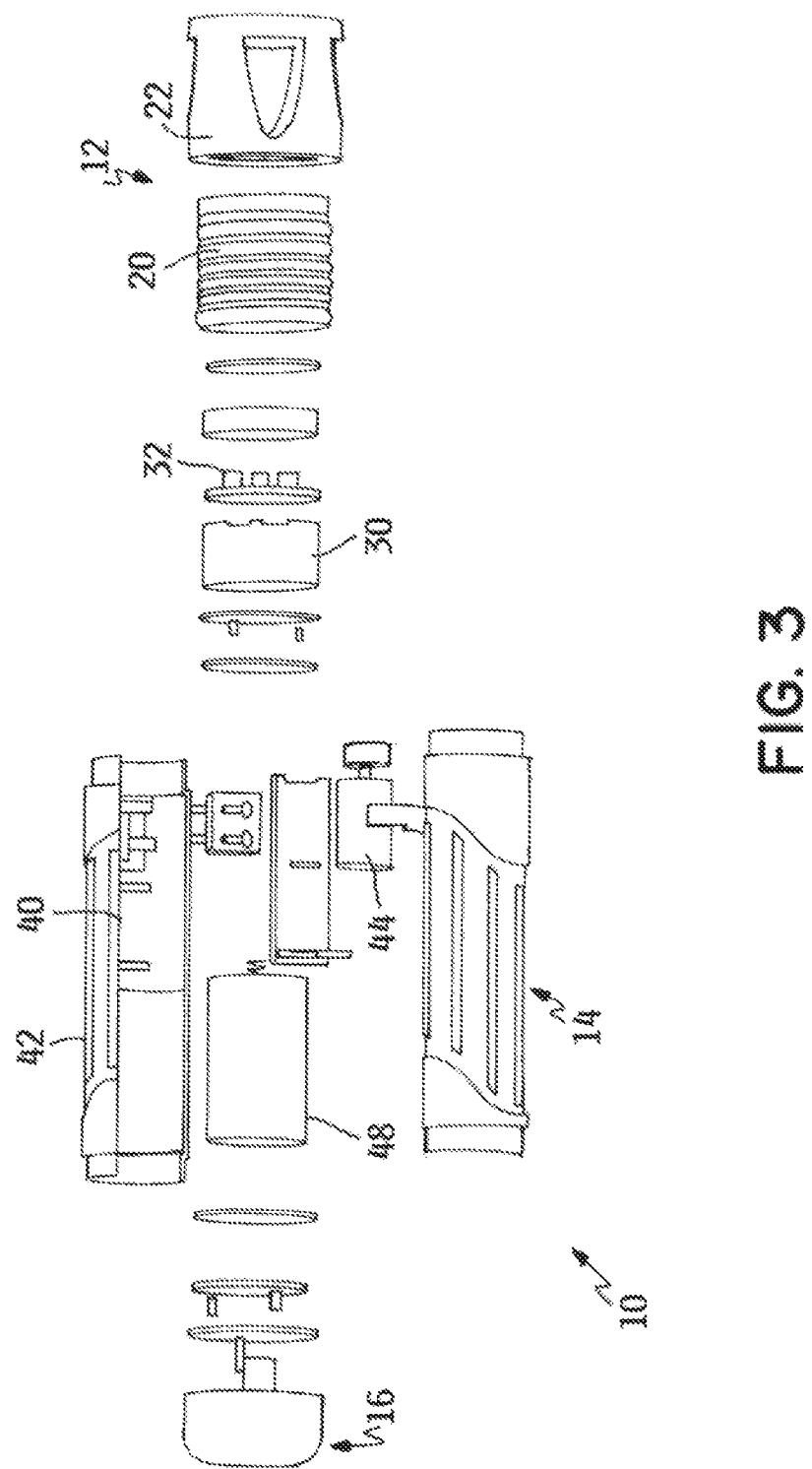
FIG. 3 is an exploded side view of the portable LED-laser biomagnetic waves therapy device.

Inside the head unit 12 a plurality of magnets 30 are provided, as illustrated in FIG. 3. In certain embodiments, the magnets 30 may be arranged in 6 columns of 7 magnets each totaling 42 magnets. The total strength of the magnets 30 may be about 4,000 gauss.

In one configuration illustrated in FIG. 6, the head unit 12 includes 20 red LEDs 32 having a wavelength of about 660 nm and 4 blue LEDs 34 having a wavelength of about 440 nm. In another configuration illustrated in FIG. 7, the head unit 12 includes 9 blue LEDs 34 having a wavelength of about 440 nm. The base and round sidewall of the light should be chromium nickel for better reflection.

The body portion 14 may be formed with a substantially cylindrical shape. Proximate opposite ends of the body portion 14, a neck may be provided to facilitate attaching the head unit 12 and the bottom cap portion 16 to the body portion 14.

The neck proximate the top of the body portion 14 may have threads formed therein to facilitate engaging the head unit 12. The neck proximate the bottom of the body portion 14 may have threads formed therein to facilitate engaging the bottom cap portion 16.

Inside the body portion 14 two chambers 40, 42 may be provided. A top chamber 40 may have an electric motor 44 and a vibrating ball mounted therein. The motor base/holders may have a thin rubber design or any spongy material between them and the motor 44 to prevent unnecessary noise and enhance comfort when holding the portable LED-laser biomagnetic waves therapy device 10.

Beneath the top chamber 40 is the second chamber 42 where the batteries 48 may be placed. In certain embodiments, the portable LED-laser biomagnetic waves therapy device 10 may be powered using four AA rechargeable batteries. The batteries 48 should be sufficiently strong enough to power the operation of the motor 44 and the LED lights 32, 34 at the same time.

A spongy cover may be placed at least partially over the body portion 14. The cover should fit tightly on the body portion 14 while permitting the body portion 12 to slide out. An outer surface of the spongy cover may have a plurality of grooves formed therein to facilitate holding the portable LED-laser biomagnetic waves therapy device 10.

The bottom cap portion 16 may serve two roles holding the batteries 48 and may include at least one aperture that enables the portable LED-laser biomagnetic waves therapy device 10 to be connected to a charger. Alternatively, controls for the operation of the portable LED-laser biomagnetic waves therapy device 10 may be positioned on a side surface of the device.

The bottom cap portion 16 may be fabricated from strong and flexible plastic to prevent cracks or breaks in the event the portable LED-laser biomagnetic waves therapy device 10 falls on a hard surface.

In certain embodiments, the portable LED-laser biomagnetic waves therapy device 10 includes a vibration power button 100, a vibration frequency control button 102, a vibration frequency display 108, an illumination power button 104 and an illumination mode control button 106. The control buttons may be recessed to facilitate a person accurately identifying a location of the control buttons without the need to look at the control buttons. In certain embodiments, the vibration control and the illumination control are associated with a single button.

Pressing the vibration power button 100 causes the vibration system to turn off. Pressing the vibration frequency control button 102 causes the vibration frequency to change and such changed frequency is displayed in the vibration frequency display 108. Alternatively, it is possible to combine the vibration power button 100 and the vibration frequency control button 102.

Pressing the illumination power button 104 causes the illumination system to turn off. Pressing the illumination mode control button 106 causes the illumination mode to change between always on and at least one flickering pattern.

A storage container (not shown) may be provided for use with the portable LED-laser biomagnetic waves therapy device 10. The storage container may include a base portion and a lid portion that are operably attached to each other. To facilitate organization of the components, the storage container may have a plurality of recesses formed therein that are each adapted to partially receive one of the components.

To facilitate recharging the batteries, a charging base may be provided. The charging base may have a recess formed therein that is adapted to receive a portion of the portable LED-laser biomagnetic waves therapy device 10.

It is also possible to use a cosmetic cover 110 (such as is illustrated in FIG. 7) in conjunction with the portable LED-laser biomagnetic waves therapy device 10. The cosmetic cover 110 may be attached to the head cover 22 to facilitate use of the portable LED-laser biomagnetic waves therapy device 10 with the cosmetic cover 110 attached thereto.

In certain embodiments, the costmetic cover 110 is removably attached to the portable LED-laser biomagnetic waves therapy device 10. A person of skill in the art will appreciate that a variety of techniques may be used to attach the cosmetic cover 110 to the portable LED-laser biomagnetic waves therapy device 10.

At least a portion of the cosmetic cover 110 may be fabricated from a transparent or opaque material so that light emitted from the LED lights 32, 34 passes through the cosmetic cover 110. In certain embodiments, substantially all of the cosmetic cover 110 is fabricated from a transparent material.

Figure 13:
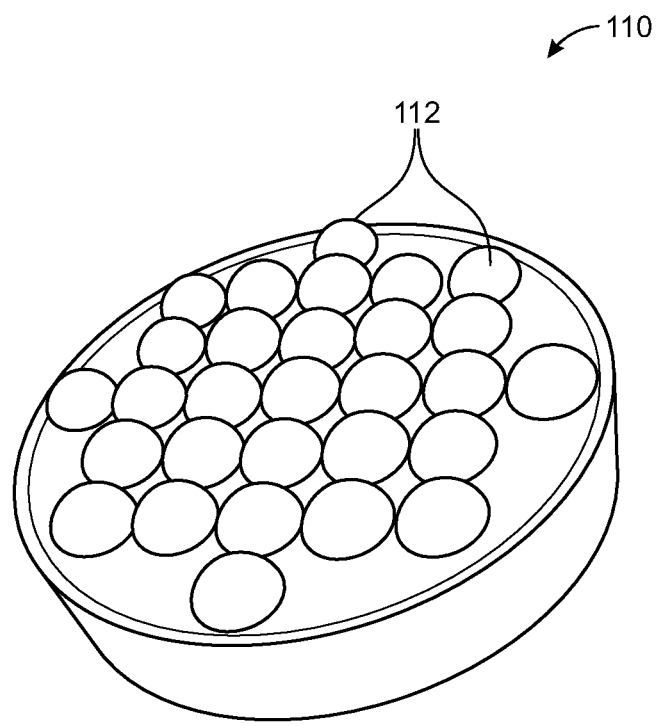
FIG. 13 is a perspective view of a cosmetic cover for use in conjunction with the portable LED-laser biomagnetic waves therapy device.
Figure 14:
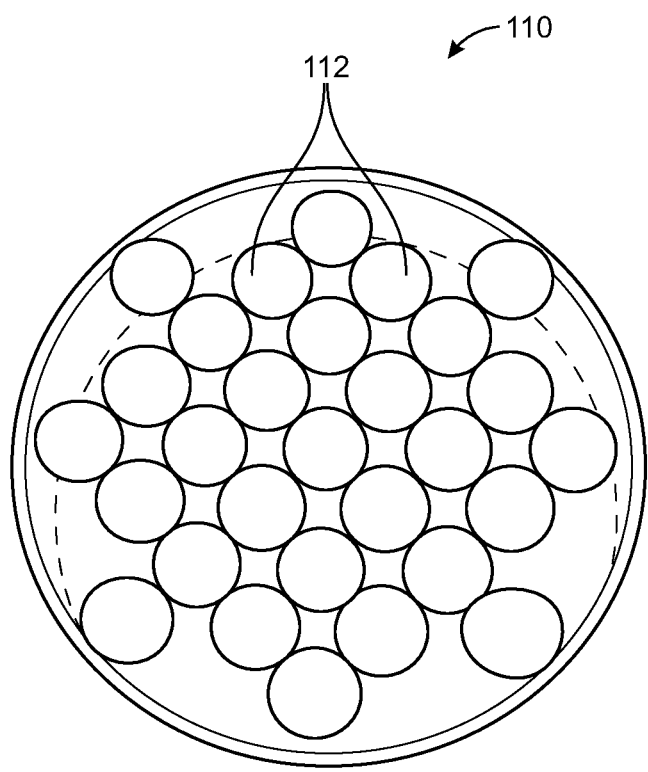
FIG. 14 is a top view of the cosmetic cover.

An upper surface of the cosmetic cover 110 may include a plurality of magnifying bubbles 112 that increase the power of the LED lights 32, 34. The magnifying bubbles 112 may extend above a surface of the cosmetic cover 110 as illustrated in FIGS. 13 and 14. This configuration may enable the magnifying bubbles 112 to provide a vibrating action as the portable LED-laser biomagnetic waves therapy device 10 is moved over the user's skin.

Figure 8:
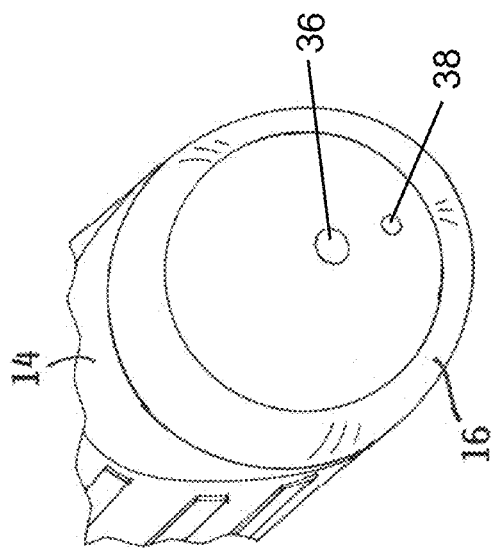
FIG. 8 is an end view of a bottom cap portion of the portable LED-laser biomagnetic waves therapy device.
Figure 9:
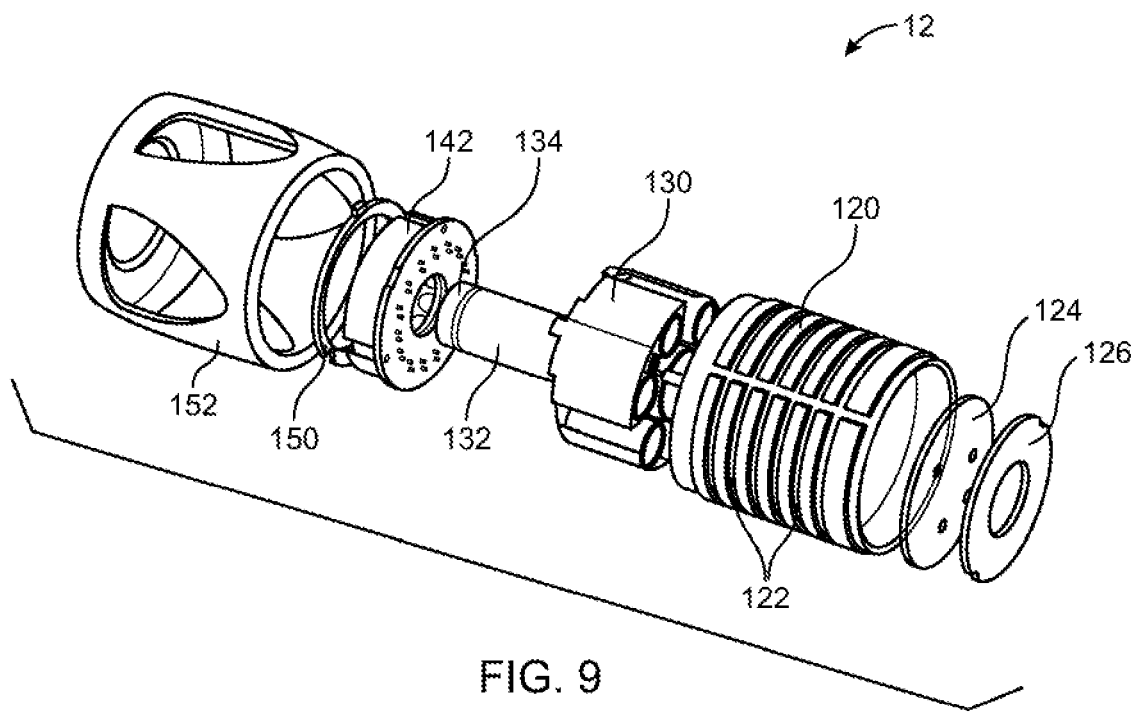
FIG. 9 is a first exploded view of another embodiment of the head unit for the portable LED-laser biomagnetic waves therapy device.
Figure 10:
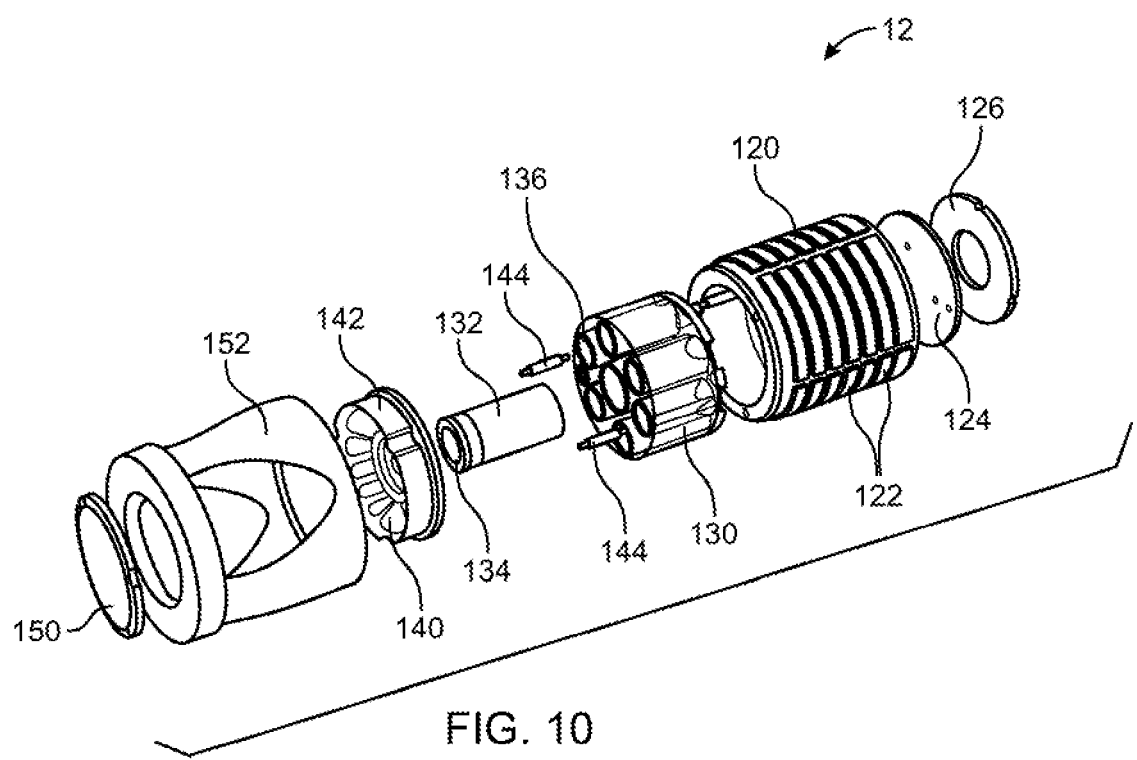
FIG. 10 is a second exploded view of the head unit of FIG. 9.
Figure 11:
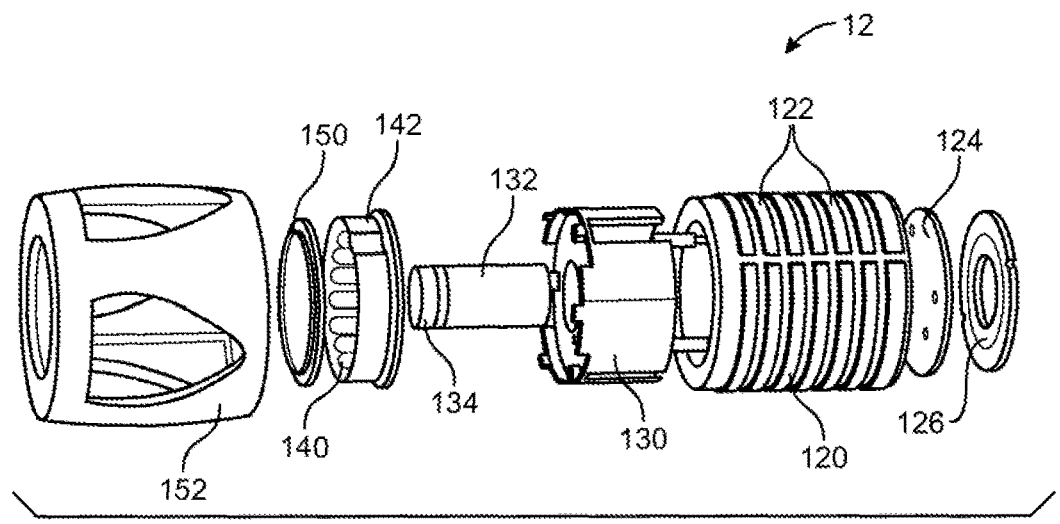
FIG. 11 is a side exploded view of the head unit of FIG. 9.
Figure 12:
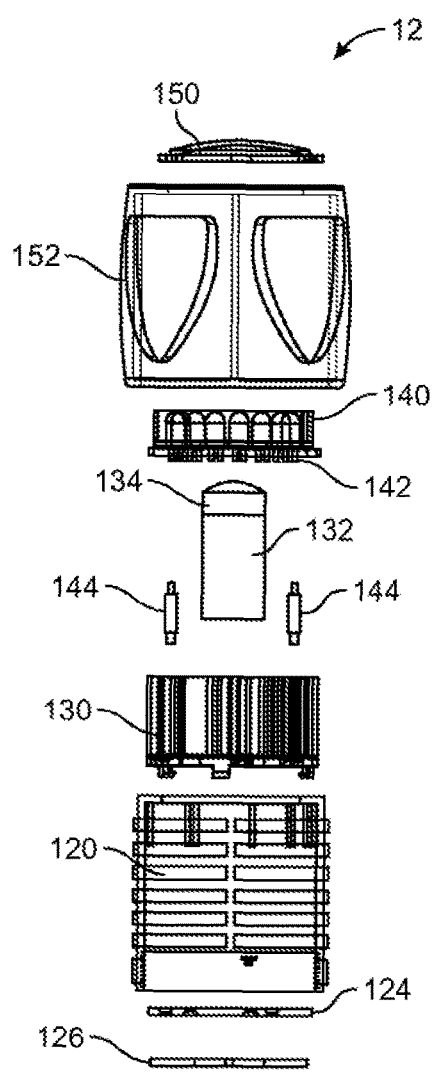
FIG. 12 is another side exploded view of the head unit of FIG. 9.

The lower end of the portable LED-laser biomagnetic waves therapy device 10 may include a charging connector 36 and a battery status indicator 38 as illustrated on FIG. 8. The battery status indicator 38 may display a color that is indicative of the level of the battery charge or may display an numeric value that indicates that level of the battery charge.

The upper surface of the cosmetic cover 110 may have a slightly concave shape. This configuration enables a user to place a cosmetic preparation such as skin cream in the concave region. The concave region thereby enhances the ability of the cosmetic preparation to remain in the cosmetic cover 110 as the cosmetic cover 110 is moved over the user's skin. The cosmetic cover 110 thereby enhances the ability that the cosmetic preparation will be massaged into the user's skin.

Another embodiment of the invention is illustrated in FIGS. 9-12. This embodiment may include an entire device or it may include a head unit that is attached to the device described in other portions of this application. In certain embodiments, the color of light emitted by the LED's in this embodiment is red.

The head unit 12 includes a head casing 120 having a recess formed therein that is adapted to receive at least a portion of the components associated with the head unit 12. In certain embodiments, an outer surface of the head unit 12 may have a plurality of ridges 122 on an outer surface thereof. The ridges 122 enhance the ability of the user to grasp the device 10. As illustrated in the drawings, the ridges 122 may be positioned in a spaced-apart configuration.

Proximate the proximal end of the head unit 12, a magnet housing lid 124 may be attached to the head casing 120. The magnetic housing lid 124 may be attached to the head casing 120 to retain the components in the head casing 120. The head unit 12 may also include an end cap 126 that is positioned over the magnet housing lid 124.

A magnet housing 130 is positioned in the distal end of the head casing 120. The magnet housing 130 has a plurality of openings formed therein. In certain embodiments, there are six openings. Each of the openings is adapted to receive at least one magnet 136. In certain embodiments, each opening receives seven magnets 136 that are positioned in a stacked configuration. The magnets 136 may be oriented offset from but generally parallel to a central axis of the head unit 12. The number and strength of the magnets 136 can be selected based upon a variety of factors.

Proximate a center of the magnet housing 130, the magnet housing has an aperture formed therein. The aperture is adapted to receive a laser 132. A prismatic splitter 134 may be mounted with respect to the end of the laser 132 from which the low level light is emitted.

The LED lights 140 are operably attached to a support board 142. In certain embodiments, the LED lights 140 are mounted in a spaced-apart configuration on the support board 142. The number, intensity and color of the LED lights may be varied based upon the intended treatment process.

At least one connector 144 may be used to attach the support board 142 to the magnet housing 130. In certain embodiments, the support board 142 may be maintained in a spaced-apart relationship with respect to the distal end of the magnet housing 130.

A lens 150 may be placed over the LED lights 140 to protect the LED lights 140 from damage such as when the device 10 is moved over a person's skin during the treatment. The lens 150 may be generally transparent so that light emitted by the LED lights 140 and the laser passes therethrough. In certain embodiments, the lens 150 may include a convex outer surface. This convex outer surface may enhance the ability to hold the device 10 in different angular orientations with respect to a person's skin.

A head cover 152 may extend over at least a portion of the head casing 120. The head cover 152 may have at least one opening formed therein. In certain embodiments, the head cover 152 has one top opening, one bottom opening and four side openings. The head cover 152 may be fabricated from a soft plastic/rubber that enhances the ability of the person using the device 10 to hold onto the device 10.

Figure 15:
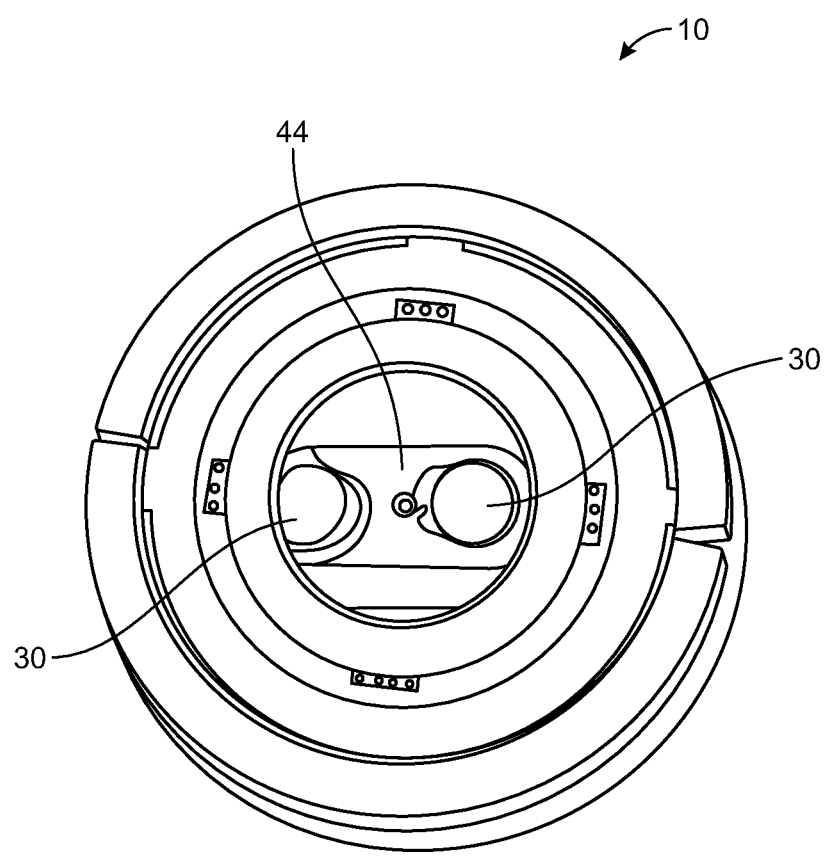
FIG. 15 is a top view of the portable LED-laser biomagnetic waves therapy device with a head unit removed therefrom.

The device may utilize a spiral magnetic field that enahnce penetration into the body of the patient to enhance the treatment effectiveness by placing at least one magnet on the output shaft of the motor 44, as illustrated in FIG. 15. The magnets 30 can be associated with the vibration head that is attached to the motor shaft. The magnets may be spaced at different distances from the center of the motor shaft The device provides therapeutic action through the combination of vibration frequencies, magnetic waves, light and laser splitting beams. Through the combination of these elements, the device provides an enhanced ability to treat pain more deeply beneath the skin and to treat pain over a larger area than the prior device.

The use of laser beam in conjunction with the light from the LEDs decreases the amount of time to achieve pain reduction. The device exhibits a "welding effect" on the stem cells in the damaged area to decrease the time for the cells to heal.

The combination of treatment elements discussed above enhances the ability of the device to exhibit beneficial results even when the device is not in contact with the skin. For example, the device can produce the beneficial results when the distal end of the device is proximate to the skin surface. As used herein, proximate means that the distal end of the device is less than about two inches from the skin surface. In other embodiments, the distal end of the device is less than about one inch from the skin surface.

Using the device with a separation from the skin surface is desirable particularly where there is damage to the skin surface or beneath the skin surface such that contact between the distal end of the device and the skin surface is likely to cause increased pain for the person on which the device is being used. Examples of such situations include a wound or burn on the surface of the skin or a broken bone beneath the skin surface.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A portable LED-laser biomagnetic waves therapy device comprising:
   a body portion;
   a head portion that is attachable to an end of the body portion;
   a vibrating mechanism mounted to at least one of the body portion and the head portion,
   wherein the vibrating mechanism comprises:
      a motor having a shaft; and
      a vibration head that is attached to the motor shaft;
   a first plurality of magnets mounted to the vibration head at different distances from a center of the motor shaft;
   a second plurality of magnets that comprises a plurality of columns of magnets;
   a magnet housing mounted in the head portion, wherein the magnet housing has a plurality of openings formed therein that are each adapted to receive one of the plurality of columns of magnets and wherein the plurality of openings are arranged in a circular pattern;
   a plurality of LEDs mounted to at least one of the body portion and the head portion;
   a laser mounted to at least one of the body portion and the head portion; and
   a power mechanism that is operably attached to the plurality of LEDs, the laser and the vibrating mechanism, wherein upon activation of the power mechanism vibrations are emitted by the vibrating head and spiral magnetic waves are emitted from the first plurality of magnets.

2. The portable LED-laser biomagnetic waves therapy device of claim 1, and further comprising a prismatic splitter associated with the laser.

3. The portable LED-laser biomagnetic waves therapy device of claim 1,
   wherein the magnet housing has an aperture formed therein that is adapted to receive the laser;
   and wherein the portable LED-laser biomagnetic waves therapy device further comprises:
   an LED mount to which the plurality of LEDs are mounted, wherein the LED mount has an aperture formed therein that is adapted to receive the laser.

4. The portable LED-laser biomagnetic waves therapy device of claim 1, wherein the second plurality of magnets have a total strength of about 4,000 gauss.

5. The portable LED-laser biomagnetic waves therapy device of claim 1, wherein the plurality of LEDs comprises a first group of LEDs and a second group of LEDs, wherein the first group of LEDs emit light at a different wavelength than the second group of LEDs, wherein the first group of LEDs are capable of emitting light at a wavelength of about 660 nm and wherein the second group of LEDs are capable of emitting light at a wavelength of about 440 nm.

6. The portable LED-laser biomagnetic waves therapy device of claim 1, and further comprising a cosmetic cover attached to at least one of the body portion and the head portion, wherein at least a portion of the cosmetic cover is transparent and wherein a plurality of convex bubbles extend from the cosmetic cover.

7. The portable LED-laser biomagnetic waves therapy device of claim 1, wherein the head portion is removably attached to the body portion and wherein the head portion has a plurality of grooves formed in an outer surface thereof.

8. The portable LED-laser biomagnetic waves therapy device of claim 1, and further comprising a switch mechanism that is capable of controlling the operation of at least one of the plurality of LEDs and the laser.

9. The portable LED-laser biomagnetic waves therapy device of claim 1, and further comprising a head cover that extends over at least part of the head portion, wherein the head cover has a plurality of openings formed therein through which the head portion is visible.

10. The portable LED-laser biomagnetic waves therapy device of claim 9, wherein an end of the head cover that is opposite the body portion has a plurality of grooves formed therein.

11. A portable LED-laser biomagnetic waves therapy device comprising:
   a body portion;
   a head portion that is attachable to an end of the body portion, wherein the head portion has a plurality of grooves formed in an outer surface thereof;
   a vibrating mechanism mounted to at least one of the body portion and the head portion,
   wherein the vibrating mechanism comprises:
      a motor having a shaft; and
      a vibration head that is attached to the motor shaft;
   a magnet housing mounted in the head portion;
   a plurality of magnets that comprises a first plurality of magnets and a second plurality of magnets, wherein the first plurality of magnets is mounted to the vibration head at different distances from a center of the motor shaft and wherein the second plurality of magnets is mounted in the magnet housing;
   a plurality of LEDs mounted to at least one of the body portion and the head portion;
   a laser mounted to at least one of the body portion and the head portion;
   a power mechanism that is operably attached to the plurality of LEDs, the laser and the vibration mechanism;
   a head cover that extends over at least part of the head portion on which the plurality of grooves are located, wherein the head cover has a plurality of openings formed therein through which the head portion is visible; and
   a resilient cover that extends over at least a portion of the body portion, wherein upon activation of the power mechanism vibrations are emitted by the vibrating head and spiral magnetic waves are emitted from the plurality of magnets.

12. The portable LED-laser biomagnetic waves therapy device of claim 11, and further comprising a prismatic splitter associated with the laser.

13. The portable LED-laser biomagnetic waves therapy device of claim 11,
   wherein the magnet housing has an aperture formed therein that is adapted to receive the laser; and
   wherein the portable LED-laser biomagnetic waves therapy device further comprises:
   an LED mount to which the plurality of LEDs are mounted, wherein the LED mount has an aperture formed therein that is adapted to receive the laser.

14. The portable LED-laser biomagnetic waves therapy device of claim 11, wherein the head portion is removably attached to the body portion with a thread mechanism and wherein the portable LED-laser biomagnetic waves therapy device further comprises a switch mechanism that is capable of controlling the operation of at least one of the plurality of LEDs and the vibrating mechanism.

15. A method of treating pain comprising:

providing a portable LED-laser biomagnetic waves therapy device comprising a body portion, a head portion, a magnet housing, a plurality of magnets, a vibration mechanism, a plurality of LEDs, a laser and a power mechanism, wherein the head portion is attachable to an end of the body portion, wherein the vibrating mechanism is mounted to at least one of the body portion and the head portion, wherein the vibrating mechanism comprises a motor and a vibration head, wherein the motor has a shaft, wherein the vibration head is attached to the motor shaft, wherein magnet housing is mounted in the head portion, wherein the plurality of magnets comprises a first plurality of magnets and a second plurality of magetns, wherein the first plurality of magnets is mounted to the vibration head at different distances from a center of the motor shaft, wherein the second pluraltiy of magnets is mounted in the head portion, wherein the plurality of LEDs is mounted to at least one of the body portion and the head portion, wherein the laser is mounted to at least one of the body portion and the head portion and wherein the power mechanism is operably attached to the plurality of LEDs and the laser;

activating the plurality of LEDs and the laser with the power mechanism to cause light to be emitted therefrom;

positioning the portable LED-laser biomagnetic waves therapy device proximate a human body that is experiencing pain beneath the skin surface so that the light from the LEDs and the laser impinge upon the human body to cause a decrease in the pain;

emitting vibrations from the vibrating mechanism to decrease the pain in the human body; and emitting spiral magnetic waves from the first plurality of magnets.

16. The method of claim 15, wherein the portable LED-laser biomagnetic waves therapy device does not contact the human body when the light from the LEDs and the laser impinge upon the human body.

17. The method of claim 15, and further comprising splitting the light emitted from the laser with a prismatic splitter.

* * * * *